(12) United States Patent
Honigmann et al.

(10) Patent No.: US 11,299,700 B1
(45) Date of Patent: Apr. 12, 2022

(54) BIOREACTOR CONTAINERS AND METHODS OF GROWING HAIRY ROOTS USING THE SAME

(71) Applicant: Acequia Biotechnology, LLC, Yuma, AZ (US)

(72) Inventors: Rocio S. Honigmann, Newbury Park, CA (US); Jaime Flores-Riveros, Newbury Park, CA (US); Martin Sierra-Honigmann, Newbury Park, CA (US)

(73) Assignee: ACEQUIA BIOTECHNOLOGY, LLC, Yuma, AZ (US)

( * ) Notice: Subject to any disclaimer, the term of this patent is extended or adjusted under 35 U.S.C. 154(b) by 0 days.

(21) Appl. No.: 17/180,489

(22) Filed: Feb. 19, 2021

(51) Int. Cl.
C12M 1/12 (2006.01)
C12N 5/04 (2006.01)
C12M 3/06 (2006.01)
C12M 1/24 (2006.01)

(52) U.S. Cl.
CPC ............ *C12M 25/14* (2013.01); *C12M 23/04* (2013.01); *C12M 23/06* (2013.01); *C12M 23/08* (2013.01); *C12M 25/06* (2013.01); *C12M 27/14* (2013.01); *C12N 5/04* (2013.01)

(58) Field of Classification Search
CPC .............................. C12M 25/14; C12M 23/08
See application file for complete search history.

(56) References Cited

U.S. PATENT DOCUMENTS

| | | | |
|---|---|---|---|
| 5,413,928 A | 5/1995 | Weathers et al. | |
| 5,423,603 A | 6/1995 | Reynolds et al. | |
| 5,698,423 A | 12/1997 | Holowach-Keller et al. | |
| 5,846,829 A | 12/1998 | Worden et al. | |
| 5,902,618 A | 5/1999 | Haasis, Jr. | |
| 5,998,162 A | 12/1999 | Cappelletti et al. | |
| 6,040,498 A | 3/2000 | Stomp et al. | |
| 6,190,913 B1 | 2/2001 | Singh | |
| 6,544,788 B2 | 4/2003 | Singh | |
| 6,589,765 B1 | 7/2003 | Choi et al. | |
| 6,589,780 B2 | 7/2003 | Banerjee et al. | |
| 6,740,526 B1 | 5/2004 | Curtis | |
| 6,753,178 B2 | 6/2004 | Adelberg et al. | |
| 6,794,183 B2 | 9/2004 | Wildi et al. | |
| 7,300,789 B2 | 11/2007 | Martin et al. | |
| 7,350,331 B1 | 4/2008 | Gontier et al. | |
| 7,419,808 B2 | 9/2008 | Zhang | |
| 7,531,350 B2 | 5/2009 | Shiau | |
| 7,585,617 B2 | 9/2009 | Dauner et al. | |

(Continued)

FOREIGN PATENT DOCUMENTS

AU 2006309568 B2 3/2012
AU 2012207053 B2 12/2014

(Continued)

OTHER PUBLICATIONS

Eibl R, Disposable bioreactors: the current state-of-the-art and recommended applications in biotechnology, Applied microbiology and biotechnology., Mar. 1, 2010;86(1):41-9.

(Continued)

*Primary Examiner* — Jonathan M Hurst
(74) *Attorney, Agent, or Firm* — Arent Fox LLP

(57) ABSTRACT

Bioreactors and methods of stimulating continuous growth of hairy root biomass in such bioreactors are provided.

22 Claims, 8 Drawing Sheets

(56) References Cited

U.S. PATENT DOCUMENTS

| | | |
|---|---|---|
| 7,666,677 B2 | 2/2010 | Medina-Bolivar et al. |
| 7,897,390 B2 | 3/2011 | Courtois et al. |
| 7,935,523 B2 | 5/2011 | Atehortua et al. |
| 8,114,664 B2 | 2/2012 | Weathers et al. |
| 8,329,471 B2 | 3/2012 | Houtzager et al. |
| 8,668,886 B2 | 3/2014 | Niazi |
| 8,709,794 B2 | 4/2014 | Shinohara |
| 8,889,406 B2 | 11/2014 | Van Der Heiden et al. |
| 9,228,166 B2 | 1/2016 | Barrett et al. |
| 9,464,282 B2 | 10/2016 | Moh et al. |
| 9,468,895 B2 | 10/2016 | Hart et al. |
| 9,469,671 B2 | 10/2016 | Niazi et al. |
| 9,550,971 B2 | 1/2017 | Niazi |
| 9,598,707 B2 | 3/2017 | Medina-Bolivar et al. |
| 9,631,215 B2 | 4/2017 | Houghton-Larsen et al. |
| 9,688,950 B2 | 6/2017 | Roulston |
| 9,867,861 B2 | 1/2018 | Hagay et al. |
| 9,872,448 B2 * | 1/2018 | Thakur .................. C12M 35/04 |
| 9,925,135 B2 | 3/2018 | Fournial et al. |
| 9,957,540 B2 | 5/2018 | Mikkelsen et al. |
| 9,963,669 B2 | 5/2018 | Leclerc et al. |
| 9,968,645 B2 | 5/2018 | Chan et al. |
| 10,364,413 B2 | 7/2019 | Shaaltiel et al. |
| 10,519,453 B2 | 12/2019 | Smolke et al. |
| 2002/0081731 A1 | 6/2002 | Stafford et al. |
| 2002/0164797 A1 | 11/2002 | Martin et al. |
| 2003/0082580 A1 | 5/2003 | Engler et al. |
| 2005/0032211 A1 | 2/2005 | Shaaltiel |
| 2005/0186669 A1 | 8/2005 | Ho et al. |
| 2007/0128718 A1 | 6/2007 | Courtois et al. |
| 2008/0138828 A1 | 6/2008 | Valluri et al. |
| 2009/0053762 A1 | 2/2009 | Shaaltiel |
| 2009/0280565 A1 | 11/2009 | Jolicoeur et al. |
| 2011/0014689 A1 | 1/2011 | Gandlur |
| 2011/0117538 A1 | 5/2011 | Niazi |
| 2011/0159590 A1 | 6/2011 | Shaaltiel |
| 2011/0256624 A1 | 10/2011 | Jenne |
| 2012/0329151 A1 | 12/2012 | Baskar et al. |
| 2013/0061351 A1 | 3/2013 | Boitel-Conti et al. |
| 2013/0244322 A1 | 9/2013 | Henon et al. |
| 2013/0344528 A1 | 12/2013 | Zuniga et al. |
| 2015/0093741 A1 | 4/2015 | Swanda et al. |
| 2015/0093776 A1 | 4/2015 | Yoon et al. |
| 2015/0093829 A1 | 4/2015 | Swanda et al. |
| 2015/0275169 A1 | 10/2015 | Hagay et al. |
| 2016/0152935 A1 | 6/2016 | Roosloot et al. |
| 2016/0168595 A1 | 6/2016 | Janssen et al. |
| 2016/0326476 A1 | 11/2016 | Maisch et al. |
| 2017/0314033 A1 | 11/2017 | Cornish et al. |
| 2018/0002655 A1 | 1/2018 | Patil et al. |
| 2018/0223294 A1 | 8/2018 | Nielsen |
| 2018/0251722 A1 | 9/2018 | Patil et al. |
| 2018/0273885 A1 | 9/2018 | Eisenkraetzer et al. |
| 2019/0002809 A1 | 1/2019 | Oakley et al. |
| 2019/0017009 A1 | 1/2019 | Yu |
| 2019/0040367 A1 | 2/2019 | Medina-Bolivar et al. |
| 2019/0040407 A1 | 2/2019 | Guerineau et al. |
| 2019/0048356 A1 | 2/2019 | Takos et al. |
| 2019/0203245 A1 | 7/2019 | Douchin et al. |

FOREIGN PATENT DOCUMENTS

| | | | |
|---|---|---|---|
| BE | 1021922 B1 | 1/2016 | |
| CA | 2278588 C | 2/2005 | |
| CA | 2630150 A1 | 10/2009 | |
| CA | 2709441 C | 2/2013 | |
| CN | 1167153 A | 12/1997 | |
| CN | 2270733 Y | 12/1997 | |
| CN | 2352538 Y | 12/1999 | |
| CN | 1049008 C | 2/2000 | |
| CN | 1063224 C | 3/2001 | |
| CN | 1324562 A | 12/2001 | |
| CN | 2510499 Y | 9/2002 | |
| CN | 1100144 C | 1/2003 | |
| CN | 1103372 C | 3/2003 | |
| CN | 1126818 C | 11/2003 | |
| CN | 1128215 C | 11/2003 | |
| CN | 1184309 C | 1/2005 | |
| CN | 1568669 A | 1/2005 | |
| CN | 1204246 C | 6/2005 | |
| CN | 1648240 A | 8/2005 | |
| CN | 2716273 Y | 8/2005 | |
| CN | 1232631 C | 12/2005 | |
| CN | 1254531 C | 5/2006 | |
| CN | 1807630 A | 7/2006 | |
| CN | 1807631 A | 7/2006 | |
| CN | 1303204 C | 3/2007 | |
| CN | 100338083 C | 9/2007 | |
| CN | 100360657 C | 1/2008 | |
| CN | 101113430 A | 1/2008 | |
| CN | 100393198 C | 6/2008 | |
| CN | 101358197 A | 2/2009 | |
| CN | 101402939 A | 4/2009 | |
| CN | 100494387 C | 6/2009 | |
| CN | 201358254 Y | 12/2009 | |
| CN | 201406422 Y | 2/2010 | |
| CN | 101168732 B | 6/2010 | |
| CN | 101392234 B | 11/2010 | |
| CN | 101100641 B | 12/2010 | |
| CN | 101979603 A | 2/2011 | |
| CN | 101130744 B | 5/2011 | |
| CN | 101130744 B | 7/2011 | |
| CN | 101121941 B | 9/2011 | |
| CN | 102210265 A | 10/2011 | |
| CN | 102212548 A | 10/2011 | |
| CN | 102212550 A | 10/2011 | |
| CN | 102352376 A | 2/2012 | |
| CN | 102352378 A | 2/2012 | |
| CN | 101531991 B | 5/2012 | |
| CN | 102464670 A | 5/2012 | |
| CN | 101491571 B | 6/2012 | |
| CN | 101849507 B | 6/2012 | |
| CN | 101629193 B | 8/2012 | |
| CN | 102618441 A | 8/2012 | |
| CN | 101773799 B | 11/2012 | |
| CN | 102229945 B | 11/2012 | |
| CN | 102783414 A | 11/2012 | |
| CN | 102086438 B | 12/2012 | |
| CN | 102321664 B | 4/2013 | |
| CN | 102321537 B | 8/2013 | |
| CN | 102487819 B | 9/2013 | |
| CN | 103305455 A | 9/2013 | |
| CN | 102634477 B | 10/2013 | |
| CN | 102617239 B | 11/2013 | |
| CN | 102771397 B | 11/2013 | |
| CN | 103609440 A | 3/2014 | |
| CN | 102876709 B | 4/2014 | |
| CN | 103695458 A | 4/2014 | |
| CN | 103773797 A | 5/2014 | |
| CN | 102627481 B | 6/2014 | |
| CN | 102754595 B | 6/2014 | |
| CN | 102517322 B | 7/2014 | |
| CN | 102618440 B | 7/2014 | |
| CN | 103120124 B | 8/2014 | |
| CN | 104017822 A | 9/2014 | |
| CN | 104026019 A | 9/2014 | |
| CN | 203820794 U | 9/2014 | |
| CN | 102408991 B | 11/2014 | |
| CN | 104195098 A | 12/2014 | |
| CN | 103031251 B | 1/2015 | |
| CN | 103340180 B | 1/2015 | |
| CN | 103146638 B | 3/2015 | |
| CN | 104404100 A | 3/2015 | |
| CN | 104450787 A | 3/2015 | |
| CN | 103194488 B | 4/2015 | |
| CN | 103194487 B | 5/2015 | |
| CN | 105063084 A | 11/2015 | |
| CN | 105087635 A | 11/2015 | |
| CN | 103609439 B | 12/2015 | |
| CN | 105463016 A | 4/2016 | |
| CN | 105505983 A | 4/2016 | |
| CN | 105505989 A | 4/2016 | |
| CN | 105543277 A | 5/2016 | |
| CN | 105602847 A | 5/2016 | |

(56) References Cited

FOREIGN PATENT DOCUMENTS

| | | |
|---|---|---|
| CN | 105671077 A | 6/2016 |
| CN | 105755090 A | 7/2016 |
| CN | 104472363 B | 8/2016 |
| CN | 205501326 U | 8/2016 |
| CN | 106047924 A | 10/2016 |
| CN | 206109043 U | 4/2017 |
| CN | 206127317 U | 4/2017 |
| CN | 106636242 A | 5/2017 |
| CN | 206253086 U | 6/2017 |
| CN | 104726485 B | 7/2017 |
| CN | 106916853 A | 7/2017 |
| CN | 104770304 B | 8/2017 |
| CN | 104705188 B | 9/2017 |
| CN | 107119070 A | 9/2017 |
| CN | 103667343 B | 10/2017 |
| CN | 107354123 A | 11/2017 |
| CN | 105906641 B | 12/2017 |
| CN | 107418894 A | 12/2017 |
| CN | 107517853 A | 12/2017 |
| CN | 107661720 A | 2/2018 |
| CN | 107760710 A | 3/2018 |
| CN | 105567565 B | 4/2018 |
| CN | 105210879 B | 5/2018 |
| CN | 105766653 B | 5/2018 |
| CN | 108034681 A | 5/2018 |
| CN | 104706554 B | 6/2018 |
| CN | 106085849 B | 6/2018 |
| CN | 106497994 B | 6/2018 |
| CN | 108220325 A | 6/2018 |
| CN | 104877906 B | 7/2018 |
| CN | 108441511 A | 8/2018 |
| CN | 104855288 B | 9/2018 |
| CN | 104845929 B | 10/2018 |
| CN | 105368888 B | 10/2018 |
| CN | 108707624 A | 10/2018 |
| CN | 103695462 B | 11/2018 |
| CN | 108841856 A | 11/2018 |
| CN | 108913716 A | 11/2018 |
| CN | 108949558 A | 12/2018 |
| CN | 106434288 B | 1/2019 |
| CN | 109136235 A | 1/2019 |
| CN | 109182374 A | 1/2019 |
| CN | 104372034 B | 2/2019 |
| CN | 105505990 B | 3/2019 |
| CN | 109511553 A | 3/2019 |
| CN | 109528620 A | 3/2019 |
| CN | 109566419 A | 4/2019 |
| CN | 109593705 A | 4/2019 |
| CN | 109601385 A | 4/2019 |
| CN | 109679993 A | 4/2019 |
| CN | 109735562 A | 5/2019 |
| CN | 208829690 U | 5/2019 |
| CN | 106479951 B | 6/2019 |
| CN | 109937879 A | 6/2019 |
| CN | 106497971 B | 8/2019 |
| CN | 209420590 U | 9/2019 |
| CN | 110622860 A | 12/2019 |
| DE | 10148208 A1 | 4/2003 |
| DE | 102011115869 B4 | 6/2015 |
| EA | 20503 B1 | 11/2014 |
| EP | 877546 B1 | 8/2001 |
| EP | 1498475 A1 | 1/2005 |
| EP | 1578978 B1 | 11/2006 |
| EP | 1649743 B1 | 10/2008 |
| EP | 1451290 B1 | 1/2011 |
| EP | 1037523 B1 | 10/2011 |
| EP | 3107371 A1 | 12/2016 |
| EP | 3502229 A1 | 6/2019 |
| IN | 0329/DEL/2002 A | 3/2007 |
| IN | 0549/CHE/2006 A | 11/2007 |
| IN | 207564 B | 11/2007 |
| IN | 206330 B | 10/2008 |
| IN | 225876 B | 1/2009 |
| IN | 1649/DEL/2008 A | 4/2010 |
| IN | 0897/KOL/2010 A | 9/2010 |
| IN | 244496 B | 12/2010 |
| IN | 0148/DEL/2010 A | 7/2011 |
| IN | 1782/DEL/2012 A | 12/2014 |
| IN | 2617/DEL/2014 A | 11/2016 |
| IN | 6960/CHE/2015 A | 6/2017 |
| IN | 201711023440 A | 1/2019 |
| IN | 360050 B | 3/2021 |
| JP | H06237762 A | 8/1994 |
| JP | 2011152076 A | 8/2011 |
| KR | 100290004 B1 | 2/2001 |
| KR | 100392515 B1 | 7/2003 |
| KR | 100444330 B1 | 8/2004 |
| KR | 100449810 B1 | 9/2004 |
| KR | 20040080083 A | 9/2004 |
| KR | 100533804 B1 | 12/2005 |
| KR | 100666879 B1 | 1/2007 |
| KR | 20070036770 A | 4/2007 |
| KR | 100671010 B1 | 11/2007 |
| KR | 100772117 B1 | 11/2007 |
| KR | 100772941 B1 | 11/2007 |
| KR | 100842420 B1 | 7/2008 |
| KR | 100869564 B1 | 11/2008 |
| KR | 100869565 B1 | 11/2008 |
| KR | 20090131937 A | 12/2009 |
| KR | 101065484 B1 | 9/2011 |
| KR | 20120028442 A | 3/2012 |
| KR | 101188165 B1 | 10/2012 |
| KR | 101204896 B1 | 11/2012 |
| KR | 101273385 B1 | 6/2013 |
| KR | 101358500 B1 | 2/2014 |
| KR | 20140083479 A | 7/2014 |
| KR | 101427102 B1 | 8/2014 |
| KR | 20140104400 A | 8/2014 |
| KR | 20140142447 A | 12/2014 |
| KR | 20160110743 A | 9/2016 |
| KR | 101957424 B1 | 3/2019 |
| MX | 2016015393 A | 5/2018 |
| RU | 2377296 C1 | 12/2009 |
| WO | 9323555 A1 | 11/1993 |
| WO | 1994000584 A2 | 1/1994 |
| WO | 1994020606 A1 | 9/1994 |
| WO | 9902720 A1 | 1/1999 |
| WO | 03080819 A1 | 10/2003 |
| WO | 2004033673 A2 | 4/2004 |
| WO | 2004074423 A2 | 9/2004 |
| WO | 2005080544 A2 | 9/2005 |
| WO | 2005108596 A1 | 11/2005 |
| WO | 2014167464 A1 | 10/2014 |
| WO | 2015149136 A2 | 10/2015 |
| WO | 2017144065 A1 | 8/2017 |
| WO | 2018002029 A1 | 1/2018 |
| WO | 2018178434 A1 | 10/2018 |
| WO | 2018211032 A1 | 11/2018 |
| WO | 2019006466 A1 | 1/2019 |
| WO | 2019098598 A1 | 5/2019 |
| WO | 2019110684 A1 | 6/2019 |

OTHER PUBLICATIONS

Mishra BN, Growth of hairy-root cultures in various bioreactors for the production of secondary metabolites, Biotechnology and applied biochemistry, Jan. 2008;49(1):1-0.

Srivastava S, Hairy Root Culture for Mass-Production of High-Value Secondary Metabolites, Critical Reviews in Biotechnology, Jan. 1, 2007;27(1):29-43.

Eibl R, Disposable bioreactors for plant liquid cultures at Litre-scale, Engineering in Life Sciences, Jul. 30, 2009;9(3):156-64.

Steingroewer J, Bioprocessing of differentiated plant in vitro systems, Engineering in Life Sciences. Jan. 2013;13(1):26-38.

Stiles AR, Hairy Root Culture: Bioreactor Design and Process Intensification, InBiotechnology of hairy root systems, 2013 (pp. 91-114).

Wagner F, Cultivation of Plant Tissue Cultures in Bioreactors and Formation of Secondary Metabolites, InPlant Tissue Culture and Its Bio-technological Application Springer, Berlin, Heidelberg. 1977 (pp. 245-252).

(56) References Cited

OTHER PUBLICATIONS

Choi YE, Types and Designs of Bioreactors for Hairy Root Culture, InPlantissue culture engineering Springer, Dordrecht., 2008 (pp. 161-172).

Eibl R, Design of bioreactors suitable for plant cell and tissue cultures, Phytochemistry Reviews, Oct. 1, 2008;7(3):593-8.

Eibl, Plant cell culture technology in the cosmetics and food industries current state and future trends, Applied Microbiology and Biotechnology, 2018, 102:8661-8675.

\* cited by examiner

BIOREACTOR CONTAINERS AND METHODS OF GROWING HAIRY ROOTS USING THE SAME

FIELD OF THE DISCLOSURE

The disclosure generally relates to bioreactor containers, a system of bioreactor containers, and methods of growing hairy root cell tissue using the bioreactor containers or system.

BACKGROUND

Hairy root ("HR") tissue cultures are produced as a result of exposing a plant to a particular species of gram-negative bacteria that normally reside in the soil, namely *Agrobacterium rhiozgenes*. During this exposure, the bacterium transfers DNA called Transfer (T)-DNA, normally contained within a large root-inducing (Ri) plasmid molecule, into the genome of the infected plant. The T-DNA harbors a number of genes that encode the enzymes responsible for modulating auxin and cytokinin production, two important plant hormones that regulate plant growth.

The new hormone balance at the infection site mitotically activates surrounding cells inducing the formation of hair-like proliferating roots, the so-called hairy roots (HRs). This phenotype is characterized by extensive branching, lack of geotropism and a high grow rate in the absence of exogenous hormones, since these cultures elaborate their own hormones as mentioned above. Thus, as these HR cultures grow, they can produce a significant amount of biomass.

However, industrial-scale production of high-value phytochemicals continues to be a challenge where a major limitation has been the design and scale-up of adequate bioreactors that promote, not only growth and expansion of biomass, but also the stable production of natural products and phytochemicals. Bioreactors typically consist of elaborate cell culture closed chambers equipped with a variety of connections and probes to facilitate gas exchange, culture media exchange, addition of elicitors or other agents, media sampling, temperature, flow rate, flow pressure, and presence of leaks. Each one of these connections creates a potential source of microbial contamination, wherein the offending microorganism proliferates in view of the presence of sugar in the culture media (e.g., sucrose). Under these circumstances, and given the typical short duplication time of microorganisms (e.g. bacteria, yeast, fungi), the culture is quickly overtaken by these biological contaminants, thereby compromising the viability of the hairy root cultures.

SUMMARY OF VARIOUS ASPECTS

The present disclosure provides improved bioreactors and methods of stimulating continuous growth of hairy root biomass (e.g., in an ageotropic fashion) to maximal biomass accretion.

In several aspects, the disclosure provides a bioreactor container, comprising a container housing having a plurality of side portions, a bottom portion, and a top portion, wherein the top portion is sealably connectable to the plurality of side portions to define an internal chamber. An internal wall in at least one of the plurality of side portions comprises a media exchange aperture. The bioreactor container further comprises a mesh scaffolding disposable within the internal chamber of the container housing, wherein the mesh scaffolding further comprises a series of alternating incline sections and decline sections each connected by a vertex, which form a plurality of channels spaced across the mesh scaffolding.

In other aspects, the bioreactor container further includes a first tubing member sealably connectable to the media exchange aperture and extending inside the container housing and a second tubing member sealably connectable to the media exchange aperture and extending outside the container housing.

In other aspects, the disclosure provides a method of growing hairy root tissue, comprising, placing a plurality of hairy root tissue samples on a bottom portion of a bioreactor container having a plurality of side portions, wherein the bottom portion and the plurality of side portions define an internal chamber. The method further comprises positioning a mesh scaffolding on top of the hairy root tissue samples so as to cover the samples, wherein the mesh scaffolding includes a series of alternating incline sections and decline sections each connected by a vertex, which form a plurality of channels spaced across the mesh scaffolding. The internal chamber of the bioreactor container is sealed by releasably connecting a removable top portion to the plurality of side portions. A culture medium is added to the internal chamber of the bioreactor container through a tube sealably connected to a media exchange aperture on an internal wall in one of the plurality of side portions of the bioreactor container. The bioreactor container including the plurality of hairy root tissue samples and the culture medium is placed into a controlled environment (e.g., for 6 to 12 weeks). An elicitor may be added to the bioreactor container (e.g., after the 6 to 12 weeks) to further stimulate growth, wherein the elicitor is added through the tube sealably connected to the media exchange aperture. The bioreactor container including the plurality of hairy root tissue samples, culture medium, and elicitor into are further cultured (e.g., for 1 to 2 weeks). Finally, the hairy root tissue from the bioreactor container is harvested (e.g., after the 1 to 2 weeks).

In other aspects, the disclosure provides for an apparatus for stimulating plant cultures, comprising a frame including a support member and one or more trays movably connected to the support member. Each tray further comprises: a bottom portion having a first edge and a second edge, a first flange member extending from the first edge above the bottom portion, and a second flange member extending from the second edge above the bottom portion. Each tray is configured to move between a first angled position, where the first edge is below the second edge, and a second angled position, wherein the second edge is below the first edge. A motion mechanism connected to the one or more trays is configured to move the one or more trays between the first angled position and the second angled position according to a motion profile configured to stimulate growth of the plant cultures. In other aspects, the disclosure provides for methods of growing hair root tissue using the apparatus. For example, one or more bioreactor containers described herein may be placed on the one or more trays and moved as described herein.

In one aspect, the disclosure provides a method of growing hairy root tissue, comprising: placing a plurality of hairy root tissue samples on a bottom portion of a bioreactor container having a plurality of side portions, wherein the bottom portion and the plurality of side portions define an internal chamber; positioning a mesh scaffolding on top of the hairy root tissue samples so as to cover the samples, wherein the mesh scaffolding includes a series of alternating incline sections and decline sections each connected by a vertex, which form a plurality of channels spaced across the mesh scaffolding; sealing the internal chamber of the bioreactor container by releasably connecting a removable top portion to the plurality of side portions; adding a culture medium to the bioreactor container through a tube sealably connected to a media exchange aperture formed by an internal wall in one of the plurality of side portions of the bioreactor container; moving the bioreactor containers according to a motion profile in a controlled environment; adding an elicitor to the bioreactor container to further stimulate growth through the tube sealably connected to the media exchange aperture; and removing the hairy root tissue from the bioreactor container for harvesting.

The method may further comprise loading the bioreactor container onto a tray of an apparatus, wherein the tray comprises: a bottom portion having a first edge and a second edge; a first flange member extending from the first edge above the bottom portion; and a second flange member extending from the second edge above the bottom portion, and wherein the tray is configured to move between a first angled position, where the first edge is below the second edge, and a second angled position, wherein the second edge is below the first edge.

DETAILED DESCRIPTION OF VARIOUS ASPECTS

Figure 1:
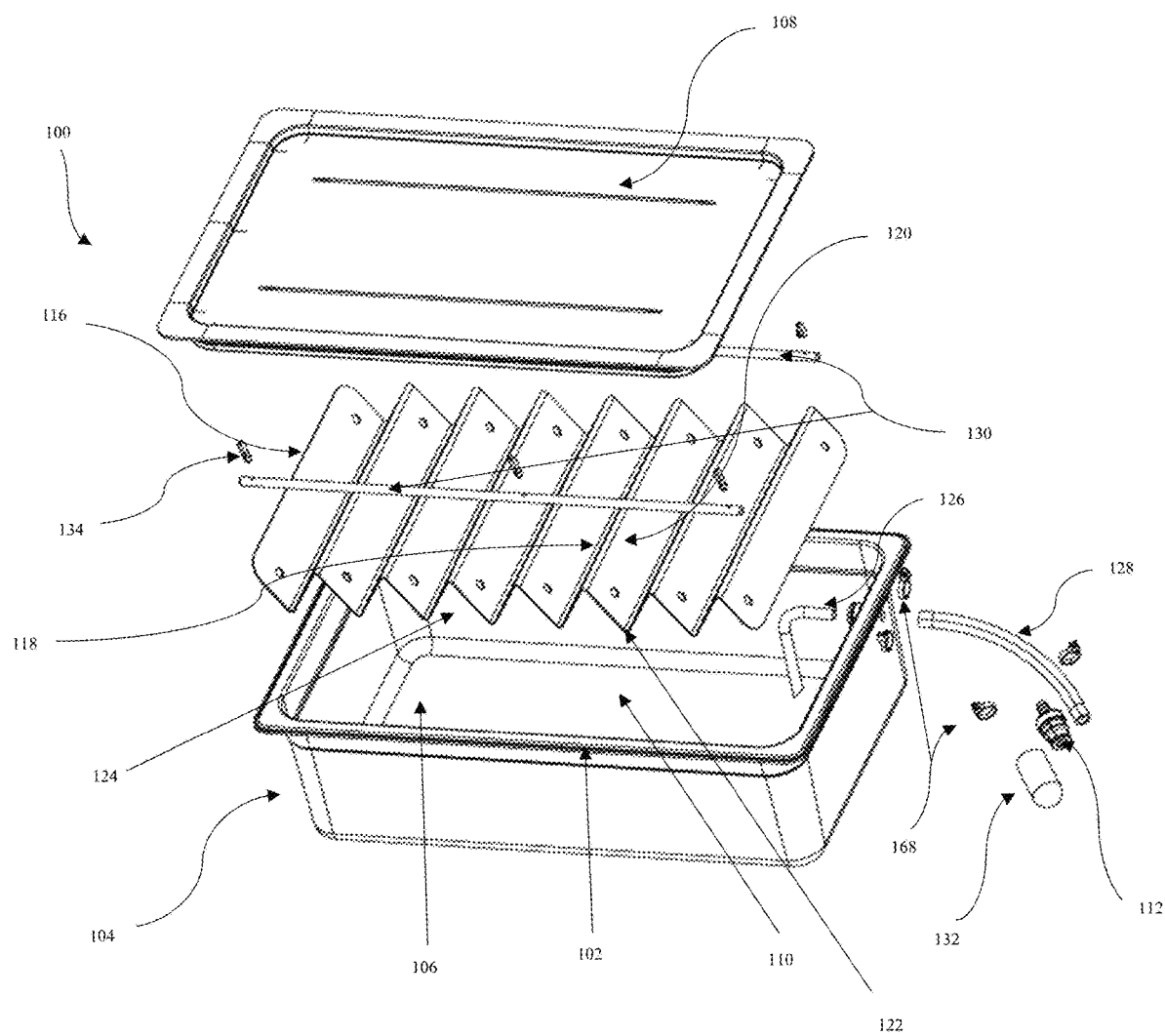
FIG. 1 is a perspective view of an exemplary bioreactor described herein.
Figure 2:
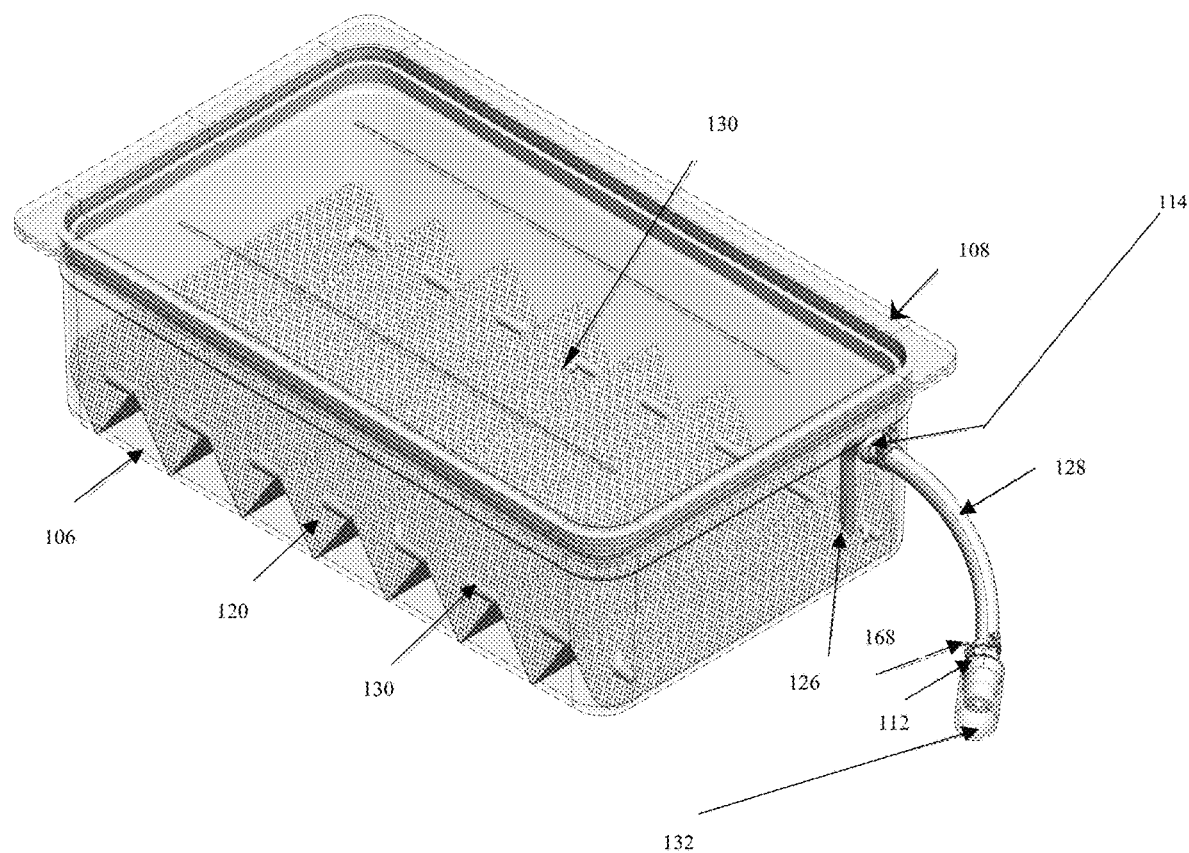
FIG. 2 is another perspective view of a bioreactor described herein.

The disclosure provides bioreactor containers, systems of bioreactor containers, methods of growing hairy roots in the bioreactor containers, an apparatus for stimulating hairy root biomass, and methods of increasing hairy root biomass using the apparatus. The bioreactor container includes a mesh scaffolding having a configuration that promotes growth of hairy roots. The bioreactor container is advantageously used in a system with other bioreactor containers and allows the user to remove or replace a bioreactor container if it becomes contaminated—without negatively affecting hairy roots grown in other bioreactor containers. This is a significant benefit over prior methods that use a single culture and/or growth system where the occurrence of microbial contamination compromises the entire cell culture batch inasmuch as the latter is contained in a single bioreactor chamber typically found with traditional industrial- or large-scale bioreactors.

The apparatus comprises one or more trays capable of holding one or more bioreactor containers described herein and/or other suitable bioreactor containers. The apparatus applies a vertical oscillation movement that promotes ageotropic growth of hairy root biomass. In particular, the apparatus enables growth in all directions, thereby increasing growth of hairy root biomass compared to traditional methods. Gravitropic sensing depends on the sedimentation of starch-filled intracellular particles (amyloplasts) within the columella cells (the primary site of gravity sensing in a root) in the direction of the gravity vector. This, in turn, determines the pattern of auxin flow in the elongation zone of a root tip thereby dictating the overall direction of growth. However, the constant reorientation of the gravity field associated with a continuous vertical motion imparted by the apparatus results in an equally continuous shifting in the direction of sedimentation of amyloplasts, which translates into a multidirectional pattern of growth, i.e., ageotropic growth.

The use of the bioreactor containers and/or apparatus allow for the formation of large-scale plant biomass growth with minimum resource depletion and creation of novel eco-sustainable plant sources to address unmet needs in nutrition, health, crop protection and personal care.

Various aspects of the disclosure are now described with reference to the drawings, wherein like reference numerals are used to refer to elements throughout. In the following description, for purposes of explanation, numerous specific details are set forth in order to promote a thorough understanding of one or more aspects of the disclosure. It may be evident in some or all instances, however, that any aspects described below can be practiced without adopting the specific design details described below.

Referring to FIGS. 1 to 3A-3D, an example of a bioreactor container 100 includes a bioreactor housing 102 for forming an environment for growing hairy root biomass. The bioreactor housing 102 may be formed from a variety of materials, such as but not limited to plastics, glass, ceramics, metals, or any material that does not negatively interact with the biomass or culturing mediums. For example, in one aspect, the bioreactor housing 102 may be a simple cost-effective reusable plastic culture container commonly used in the food preparation industry. The bioreactor housing 102 comprises a plurality of side portions 104, a bottom portion 106, and a top portion 108. The top portion 108 is configured to be sealably connectable to the plurality of side portions 104, which thereby defines an internal chamber 110 within which the environment for growing hairy root biomass may be maintained. The top portion 108 may be releasably sealed to the plurality of side portions 104, for instance, with the use of a silicon gasket fitted with an indentation running along the entire perimeter, which provides an airtight closure. In other aspects, the bioreactor containers 100 are 12" wide×20" long×6" high, although the dimensions may be adjusted to suit any particular implementation.

A mesh scaffolding 116 for supporting hairy tissue growth is configured to be removably placed within the bioreactor container 100, such as on top of hairy root (HR) cultures placed along the bottom portion 106 of the container housing 102. The mesh scaffolding 116 may be formed of a material such as, but not limited to, nylon, plastic, high density polyethylene (HDPE), polycarbonate, or any other material that provides a structure for supporting geotropic growth of the HR cultures. The mesh scaffolding 116 is defined by a series of sections that contact and extend from the HR cultures in more than one direction to help support growth. For instance, in one aspect, the mesh scaffolding 116 includes alternating incline sections 118 and decline sections 120, each connected by a vertex 122, which in turn form a plurality of channels 124 spaced across the mesh scaffolding 116.

The mesh scaffolding 116 has a shape, thickness and opening sufficient to permit HR growth. In several aspects, the mesh scaffolding 116 may be square or diamond, an opening size of 0.05" to have 0.5" and thickness of 0.03" to 0.20". For example, the mesh may be 0.083" diamond and 0.06" thickness; 0.120"×0.120" square and 0.07" thickness; 0.100" square and 0.050" thickness; 0.120"×0.120" square and 0.07" thickness, 0.125" diamond and 0.05" thickness; 0.125" square and 0.038" thickness; 0.155" square and 0.055" thickness; 0.203" square and 0.059" thickness; ¼" diamond and 0.08" thickness; ¼" square and 0.08" thickness; ¼" diamond and 0.08" thickness; ¼" diamond and 0.08" thickness; ¼" diamond and 0.095" thickness; ¼" diamond and 0.115" thickness; ¼" diamond and 0.05" to 0.09" thickness; ¼" square and 0.095" thickness; ¼" square and 0.095" thickness; ¼" square and 0.095" thickness; ¼" square and 0.095" thickness; 0.30" diamond and 0.13" thickness; 0.315" square and 0.085" thickness; 0.375" diamond and 0.20" thickness; 0.50" diamond and 0.12" thickness; 0.50" square and 0.09" thickness; ½" diamond and 0.10" thickness; ½" diamond and 0.125" to 0.190" thickness; ½" square and 0.09" thickness, ½" diamond and 0.13" thickness; 0.75" square and 0.13" thickness; ¾" diamond and 0.140" thickness; 0.75" diamond and 0.13" thickness; or 1.25" diamond and 0.14" thickness.

In some aspects, the mesh scaffolding 116 is folded in an accordion-like fashion and defines a plurality of channels 124, which run parallel to each other along a longitudinal length of the mesh scaffold 116. It should be understood, however, that the mesh scaffold 116 may have other configurations. The mesh may have the width and length of the bioreactor container (e.g., 9-12" wide by 30-40" long), and may be heat pressed to retain the desired configuration (e.g., accordion-like). The mesh may also be hole-punched near the ends for holding the supporting member 130 (e.g., rod) and tied down with the limiting members 134 (e.g., cable ties) for stability.

Figure 3A:
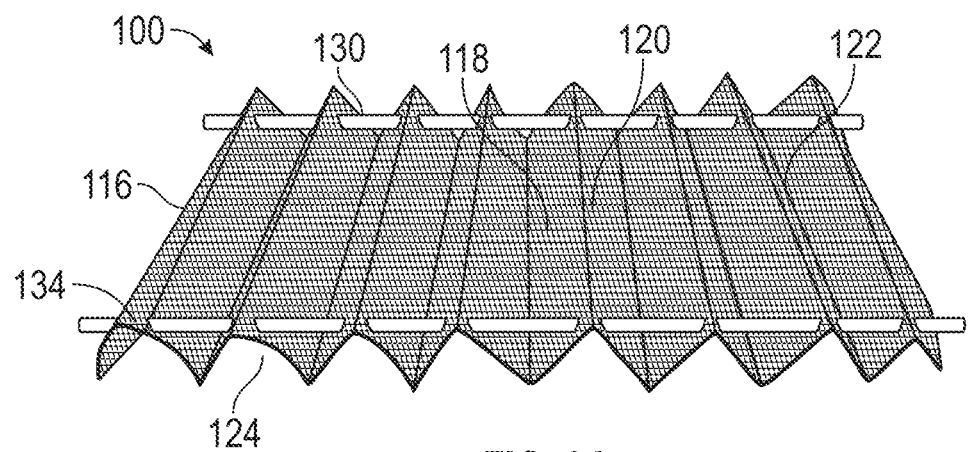
FIGS. 3A-D are up-close perspective views of various components of a bioreactor container including a mesh scaffolding (FIG. 3A), a first tubing member (FIG. 3B), and a second tubing member (FIGS. 3C and 3D).
Figure 3B:
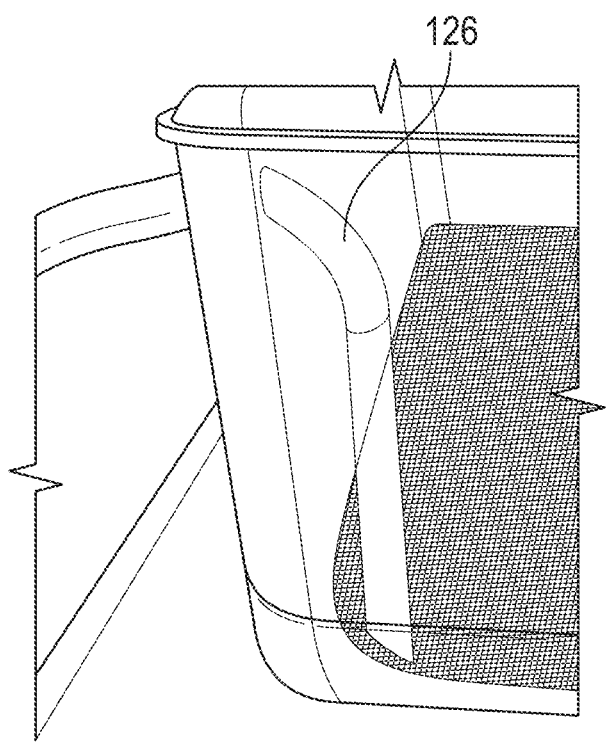
Figure 3C:
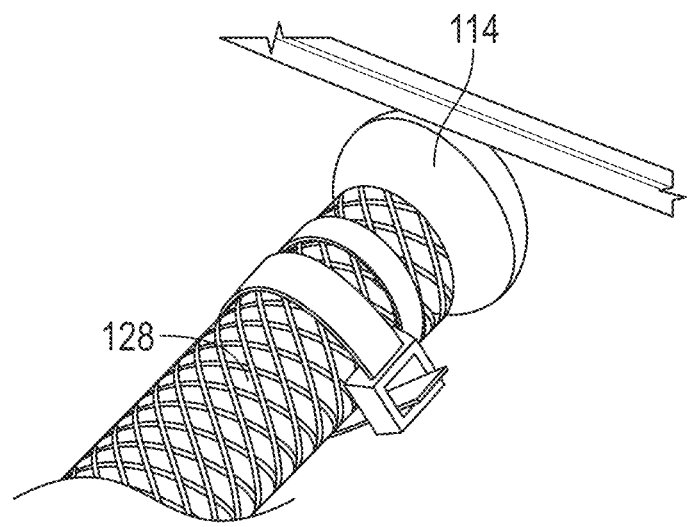
Figure 3D:
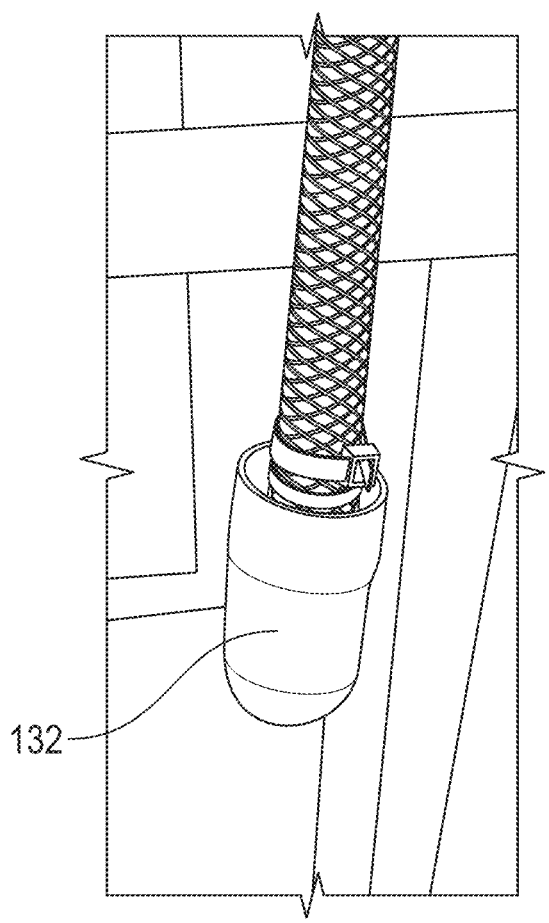

Further, in some aspects, the relative position of the incline sections 118 and decline sections 120 are maintained by running respective support members 130 through opposing longitudinal edges of the mesh scaffolding 116 (see FIG. 3A). The support members 130 may have any cross-section, e.g., round, square, and may be formed from a material having sufficient stiffness to support the mesh scaffolding 116. Suitable materials for the support members 130 may include, but are not limited to, plastics, metals, polycarbonate, nylon, and high density polyethylene. Additionally, in some cases, the support members 130 may include limiting members 134 to contain movement of the mesh scaffolding 116 along the support members 130. For instance, the limiting members 134 may be placed at each end of each support member 130 to hold the mesh scaffold 116 within a length of each support member 130. Further, one or more limiting members 134 may be placed at one or more locations along each support member 130 to help maintain a spacing between sections of the mesh scaffold 116. The limiting members 134 may have a shape, such as a washer-like structure, that extends from each support member 130 while allowing the limiting member 134 to be mounted to the support member 130. Suitable materials for forming the limiting members 134 may include, but are not limited to, an elastomer, a rubber, a plastic, or any material having sufficient static and/or dynamic friction relative to the surface of the support members 130, and relative to any force applied by the mesh scaffold 116, to enable the limiting members 134 to hold their position.

An internal wall in at least one of the plurality of side portions 104 has a media exchange aperture (e.g., a ⅜" hole) where a grommet 114 (e.g., made of silicone) is inserted that, in combination with a first tubing member 126 and a second tubing member 128, can act as an inlet or outlet to the internal chamber 110 for transporting media. The grommet 114, first tubing member 126, and second tubing member 128, are designed to allow any necessary culture media utilized during the HR biomass growth process to be pumped into the internal chamber 110 with little to no contamination from outside influences. The first tubing member 126 is connected and sealed to the grommet 114 in the internal chamber 110. In one aspect, the first tubing member 126 is an L-shaped piece of stainless steel tubing inserted through the grommet 114 with the longer end running parallel to the internal wall. The end of the first tubing member 126 in the internal chamber 110 may be cut with a beveled edge and juxtaposed to the corner at the bottom portion 106 of the container housing 102. This design allows dispensing or suctioning of culture media with minimal mechanical disruption of the HR cultures inside the container housing 102.

The second tubing member 128 is connected and sealed to the grommet 114 on the outside of the of the container housing 102. The second tubing member 128 may be a piece of medical grade reinforced silicon hose, which in turn can be connected to an Easy-Load Masterflex I/P peristaltic pump (e.g., Cole-Palmer, Model 77602-30) via a quick-connect (or disconnect) valve coupling 112. The second tubing may include a barb 168 (e.g., ⅜") for improved connections. When the pump is not in use, the second tubing member 128 protruding from the container housing 102 is sealed with a tubing cover 132 to keep it tightly closed, thereby maintaining the seal of the bioreactor container 100. This system allows dispensing or removing of liquid culture media without the need to actually open the bioreactor container 100, which is kept tightly sealed throughout the entire period of time the HR biomass continues to grow until attaining its endpoint.

Figure 4:
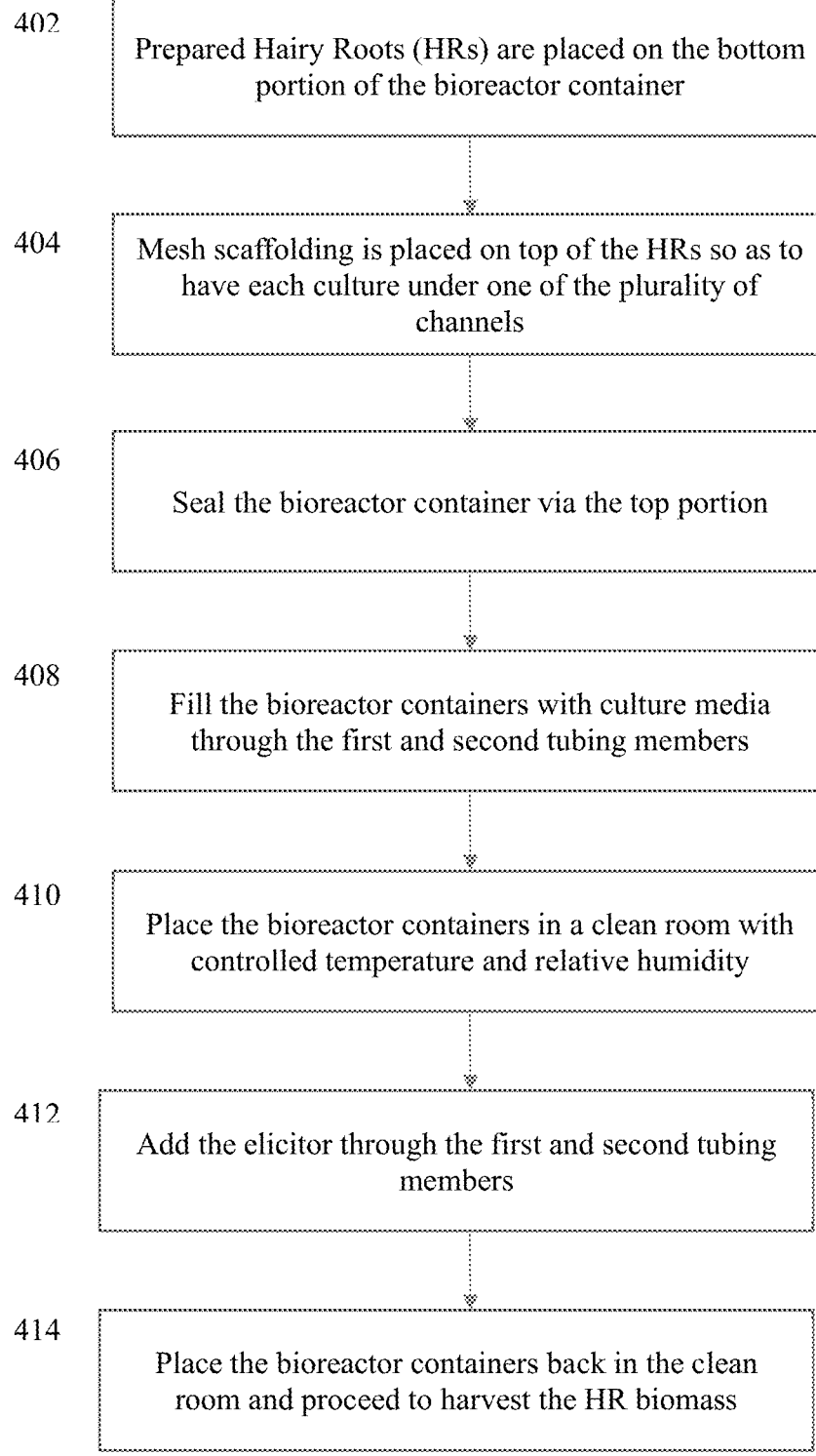
FIG. 4 is a flowchart of a method of growing hairy root cultures in a bioreactor container.

Referring to FIG. 4, the disclosure further provides a method 400 of growing HR biomass using the bioreactor container 100 described above. Prior to placing the HR cultures into the bioreactor container, preliminary steps may be undertaken to prepare the HR cultures.

For example, in preparation for HR cultures grown in the bioreactor containers, a two-step protocol is may be followed to pre-condition the tissue and acclimate to conditions for large-scale propagation. Individual hairy roots from the appropriate mother cultures are snipped individually and placed into separate wells of a sterile 6-well tissue culture plate (VWR) containing culture medium (e.g., Gamborg's B5) optimized for HR growth and kept in a temperature-controlled atmosphere (e.g., set at 25° C.). After several weeks of growth (e.g., 4 weeks), the resulting HR tissue is then transferred into plant culture cylinders (e.g., Greiner Bio-One, VWR) fitted with a physical scaffold for growth and anchoring (e.g., nylon mesh). Each of these cylinders contains culture medium (e.g., Gamborg's B5) optimized for HR growth and are incubated for several more weeks (e.g., 4 weeks) for additional growth. By the end of this period, the roots have typically attained a critical mass (e.g., approximately 100 g of aggregate biomass) suitable for transfer to the bioreactor container described herein. This operation is accomplished by extracting from the plastic cylinders the physical scaffold with the HR tissue attached to them and placing them directly on the bottom of the bioreactor containers (block 402). The multi-fold nylon mesh (116) is then lowered on top covering the support with the roots attached to them, thereby promoting continued growth of a large mass of HR tissue anchoring to the support (block 404).

At block 406, once the HR roots have been appropriately placed under the mesh scaffolding 116 the bioreactor container 102 is sealed via the top portion 108. At block 408, the bioreactors are then filled, through the first and second tubing members 126, 128, with a suitable culture medium (e.g., Gamborg's B5 culture medium) optimized for HR growth. At block 410, the bioreactor containers are kept in a clean room with controlled temperature (e.g., 25° C.) and relative humidity (e.g., 50%). It takes a total of at least 6-8 weeks for these cultures to attain approximately a 15-fold increase in biomass. At block 412, any elicitor (e.g., salicylic acid, yeast extract, dextran, pectin, chitin, fungal extract, methyl jasmonate, jasmonic acid, polyethylene glycol, proline, gibberelic acid, sorbitol, silver, cadmium, copper) is added through the first and second tubing members 126, 128, to further stimulate production of secondary metabolites that possess biological activity (bioactives). At this point, the volume of culture media may be increased. At block 414, 7-14 days after elicitor stimulation, bulk harvesting is performed by recovering both the biomass and culture media from the bioreactor chamber.

The present disclosure further provides for a system of bioreactor containers 100. Each bioreactor container 100 of the system of bioreactor containers has the elements described herein. Each bioreactor container has a separate first and second tubing members 126 and 128, respectively, and is individually sealed. This prevents any cross contamination from occurring and allows for all of the other bioreactor containers 100 to remain functioning if one bioreactor container's sample is compromised (e.g., via contamination).

Figure 5:
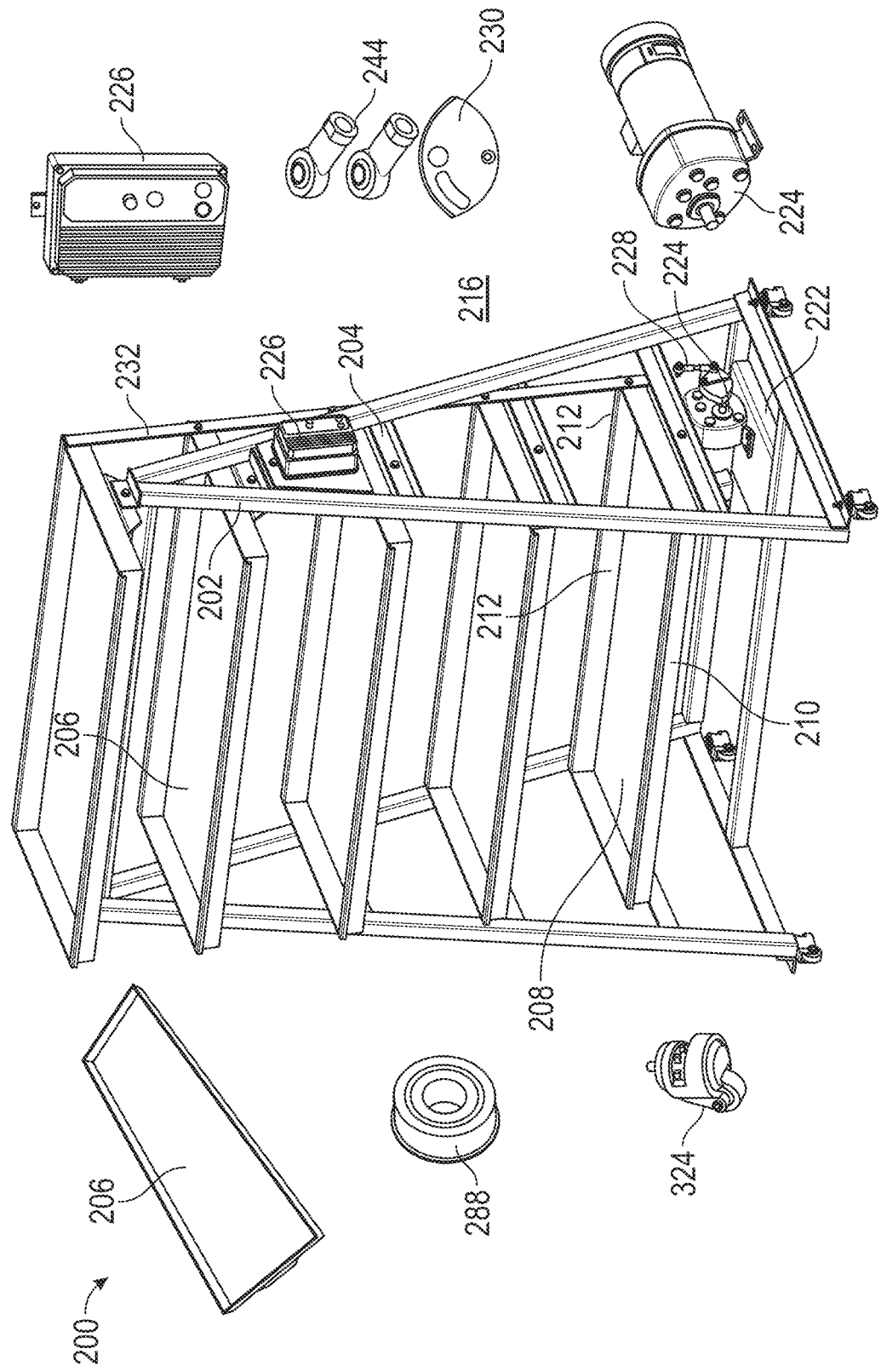
FIG. 5 is a front perspective view of an apparatus described herein for stimulating plant cultures and perspective views of various components of the apparatus.
Figure 6B:
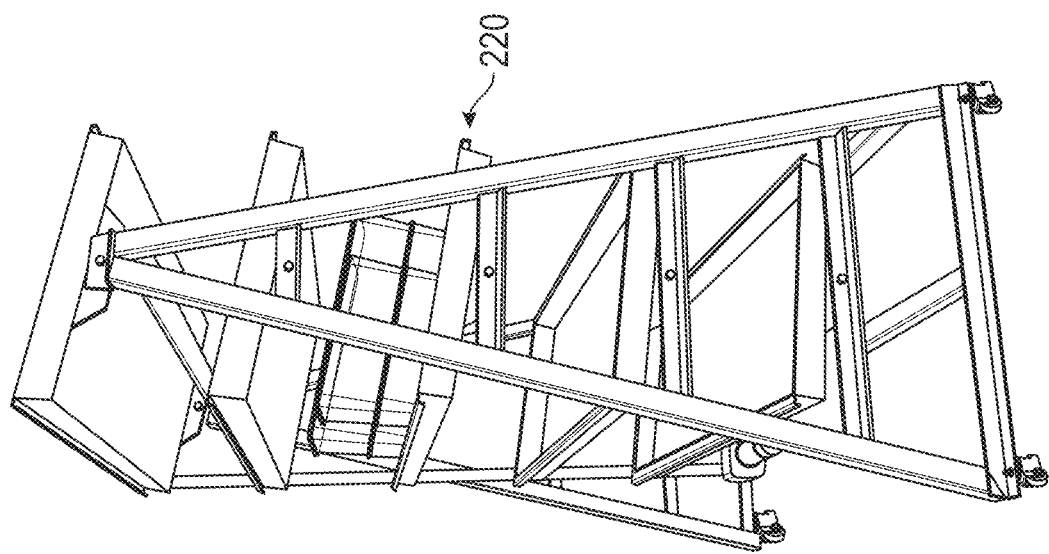
FIGS. 6A and 6B are side perspective views of an apparatus described herein comprising movable trays respectively in first and second angled positions between which the trays alternate.
Figure 6A:
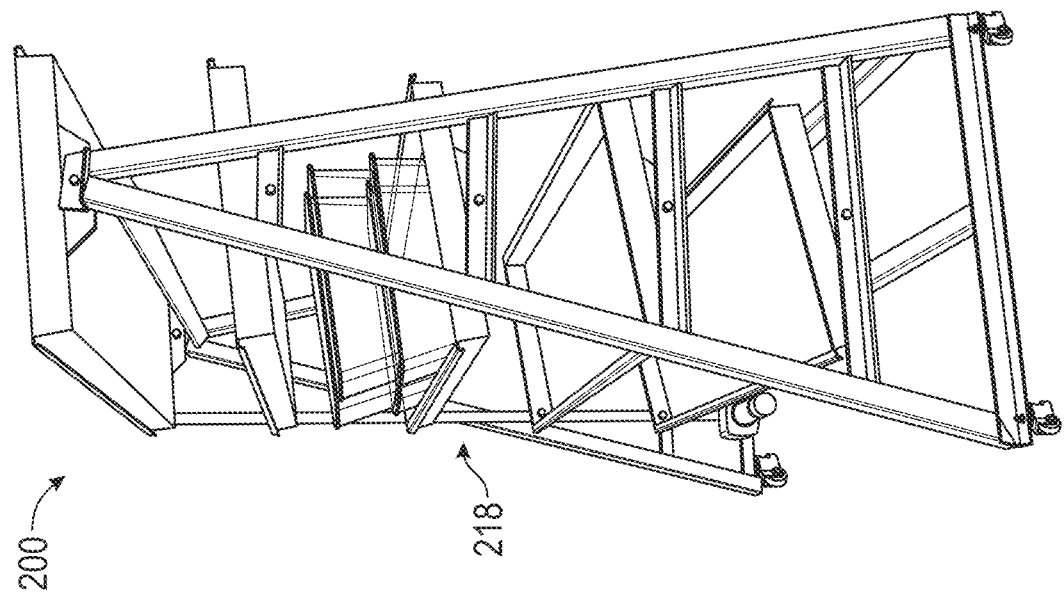

Referring to FIGS. 5, 6A, and 6B, in some aspects, the process of cultivating HR biomass can also include the use of an apparatus 200 for stimulating the plant cultures. The apparatus 200 comprises a frame 202 including a support member 204, and one or more trays 206 movably connected to the support member 204 and configured to hold one or more bioreactor containers 100. Each of the one or more trays 206 further is defined by a bottom portion 208 having a first edge 210, and a second edge 212. In some cases, the first edge 210 has a first flange member, which extends above the bottom portion 208 and the second edge 212 has a second flange member 216, which extends above the bottom portion 208, in order to contain the bioreactor container 100 on the tray 206.

Each of the one or more trays 206 is configured to move between a first angled position 218 (FIG. 6A), where the first edge 210 is below the second edge 212, and a second angled position 220 (FIG. 6B), wherein the second edge 212 is below the first edge 210. An elongated support member 232 (a tie rod) that rotatably supports each tray within the apparatus allows for the one or more trays to move between the first angled position 218 and the second angled position 220. For example, each elongated support member 232 may extend and be connected to each tray at one or more positions at the bottom of each tray along a central longitudinal axis. Further, each elongated member 232 extends beyond at least one side (optionally both sides) of each tray and may be rotatably mounted to the apparatus within a ball bearing 288.

A motion mechanism 222 is connected to the one or more trays 206. The motion mechanism is comprised by an adjustable eccentric piece (cam) that connects to a motor shaft and to one of two rod ends—the other rod end is connected to the tie rod 232. The motion mechanism is configured to move the one or more trays 206 between the first angled position 218 and the second angled position 220 according to a motion profile configured to stimulate growth of the plant cultures.

The rotating or swaying movement of bioreactor containers 100 applied by the motion mechanism 222 stimulates the growth of HR when cultures are maintained on an intermittent air-media interphase. The continuous movement between the first angled position 218 and second angled position 220 is achieved using the apparatus 200. This apparatus 200 is designed to hold a plurality (e.g., 40) culture bioreactor containers 100. The apparatus 200 may include wheels 324.

Without wishing to be bound to any theory, the continuous movement created by the apparatus 200 causes a periodic vertical shifting of amyloplasts, unique cell organelles, which provides a cellular basis for the growth stimulation. These organelles direct and stimulate the growth of statocytes, which represent cells located at the leading edge of root tips. The continuous shifting of amyloplasts inside statocytes constitutes a sensing mechanism for gravitropism, which triggers a growth signal. The rocking movement delivers a continuum of opposing signals, which results in multidirectional root growth in an ageotropic fashion.

In some aspects, the motion mechanism 222 includes a motor 224 mounted to the apparatus 200 and having a rotatable axle that connects to a transmission system 228 that in turn connects to each tray 206 to apply the motion. The transmission system 228 includes a controller plate 230, which is connected to a tie rod 232, which in turn is connected to each tray 206. The system may also include a DC driver and speed controller 228. The controller plate 230 is connected to the tie rod 232 by rod ends 244.

The controller plate 230 contains a groove takes an adjustable plant that converts the rotational motion of the motor 222, and defines the motion profile of the tie rod 232. The adjustable plate determines the motion profile of the tie rod 232, and the tie rod 232 applies the motion profile to the trays 206, and in turn to each bioreactor 100. In some aspects, the groove limits the motion of the tie rod 232 to be substantially vertical. The substantially vertical motion of the tie rod 232 in turn causes the trays to move between the first angled position 218 and the second angled position 220 by rotating them about a first axis determined by the point of attachment to the support member 204.

A variable speed drive 228 determines the rotation speed of the motor 224, and therefore the movement speed of the tie rod 232, trays 206, and bioreactor containers 100. In some aspects, the variable speed drive 226 causes the movement speed of the trays 206 to be between 5-30, 8-20, or 10-15 cycles per minute, or between 5-30, 8-20, or 10-15 movements from the first angled position 218 to the second angled position 220, and back to the first angled position 218. The variable speed drive 226 can be performed through a DC motor speed controller. The tray angle movement may also be adjustable with the cam, and may range from a 10° to 25°, such as a 10° to 20° angle or a 10° to 15° angle.

Without wishing to be bound to any theory, the growth is directly affected and stimulated by this constant motion. First, by affecting the gravitropic growth of the roots, promoting the roots growth in multiple directions simultaneously (ageotropic). Second, by the sequential and constant transition from the roots being submerged in the growth media and then exposed to the air. This promotes a balance between feeding and aeration that greatly stimulates the root growth and health.

In some aspects, the method 400 of growing the HR biomass using the bioreactor containers 100 can further include the use of the apparatus 200. After the bioreactors are filled, through the first and second tubing members 126, 128, respectively, (e.g., with Gamborg's B5 culture medium) the bioreactors placed in a clean room with controlled temperature (25° C.) and relative humidity (50%) on the apparatus 200 where they are continuously moved between the first angled position 218 and second angled position 220 for 6-8 weeks. Furthermore, when an elicitor (e.g., salicylic acid, yeast extract, dextran, pectin, chitin, fungal extract, methyl jasmonate, jasmonic acid, polyethylene glycol, proline, gibberelic acid, sorbitol, silver, cadmium, copper) is added through the first and second tubing members 126, 128, respectively, the bioreactor containers are placed on the apparatus 200 and continuously moved between the first angled position 218 and second angled position 220 for 7-14 more days. Bulk harvesting is then performed by recovering both the biomass and culture media from the bioreactor chamber as discussed herein.

It will be appreciated that in the development of any actual implementation of the present disclosure, numerous implementation-specific decisions may be made in order to achieve the developer's specific goals, and these specific goals will vary for different implementations and different developers. It is understood that such a development effort might be complex and time-consuming, but would nevertheless be a routine undertaking of engineering for those of ordinary skill in the art, having the benefit of this disclosure.

Furthermore, it is to be understood that the phraseology or terminology used herein is for the purpose of description and not of restriction, such that the terminology or phraseology of the present specification is to be interpreted by the skilled in the art in light of the teachings and guidance presented herein, in combination with the knowledge of the skilled in the relevant art(s). Moreover, it is not intended for any term in the specification or claims to be ascribed an uncommon or special meaning unless explicitly set forth as such.

The various aspects disclosed herein encompass present and future known equivalents to the known modules referred to herein by way of illustration. Moreover, while aspects and applications have been shown and described, it would be apparent to those skilled in the art having the benefit of this disclosure that many more modifications than mentioned above are possible without departing from the inventive concepts disclosed herein.

The following examples serve to illustrate certain aspects of the disclosure and are not intended to limit the disclosure.

Example 1: Biomass Growth of Hairy Root Cultures Derived from *A. indica*

An initial biomass of at least 75 g of hairy roots derived from *A. indica*, and contained on a mesh scaffolding, were transferred to the bottom of bioreactor containers. A multifold (accordion) nylon mesh was lowered on top of the biomass, thereby anchoring the hairy root tissue to the multi-fold nylon mesh, and the bioreactor containers were then placed in an apparatus described herein for continuous oscillation adjusted to 12 cycles/minute and a tilt angle of 10°. Culture media was added and biomass accretion was followed anywhere from 3-12 weeks. An elicitor (jasmonic acid) was added to further stimulate production ten days prior to biomass harvesting. Biomass yield (final biomass weight) was then recorded and the result plotted against time in culture (see FIG. 7).

Figure 7:
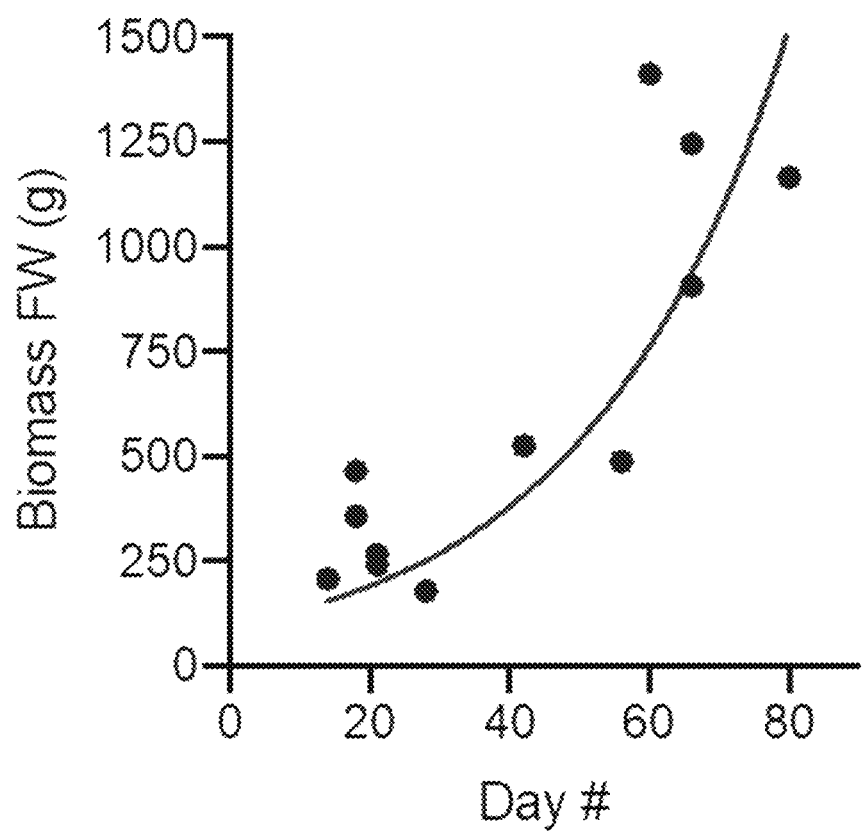
FIG. 7 is a graph showing exemplary biomass yield plotted against time in culture, as described in Example 1.

FIG. 7 shows the growth profile for several individual cultures (95 g average initial weight), which exhibit an expansion pattern that increases exponentially over time. The line represents the non-linear regression fit for the entire dataset. The data indicates that these cultures proliferate in accordance with a classical Malthusian model of population growth, which follows a geometric progression based on binary fission duplicating approximately every 20 days with a corresponding doubling of biomass. In this model, cell culture growth begins following an initial lag phase during which adaptation to the culture conditions occurs, followed by an exponential log phase where the cell mass and cell number increases exponentially and then, a subsequent growth deceleration phase begins to predominate as nutrient depletion and accumulation of toxic product start to develop. However, the depletion of nutrients and accumulation of toxic products can be controlled by regular feeding intervals, thereby maintaining the viability of the culture before cell death occurs.

The analysis suggests that the cultures should be maintained under these growth conditions for at least 80-90 days to reach 1,250-1,500 g of biomass or more.

Example 2: Production of Secondary Metabolites by Hairy Root Cultures Derived from *A. indica*

A collection of bioactive secondary metabolites produced by HR cultures derived from *A. indica* can be collected and enriched or purified using conventional and green extraction methods. These bioactives are largely represented by the limonoid family of triterpenoid compounds, which includes the azadirachtins. Limonoids have a number of advantageous effects, including antifeedant effects, as well as anti-molting or insect growth-regulating (IGR) effects in a variety of target pests. However, there are additional secondary metabolites produced by these HR cultures, including secreted bioactives, as well as volatile organo-sulfur compounds. It is possible to use macroreticular resins (e.g., Amberlite XAD resins) in the form of rigid beads to adsorb and capture these compounds, thereby facilitating their extraction from HR cultures. Using these resins, it is possible to concentrate the limonoid fraction present in the culture media.

The starting material for this operation is the HR biomass grown in the bioreactors (e.g., described in Example 1). The harvested, wet HR material is processed in a heavy-duty blender to obtain an initial homogeneous grind. A suspension is created by mixing the ground biomass with the conditioned culture media to which the non-ionic, AMBERLITE® XAD®2 resin is added (e.g., at a ratio of 20 g/L). The entire mixture is then transferred into a 30-gallon drum, where it is subjected to continuous agitation using a magnetic stirrer for at least 24-hr to promote binding of bioactives contained both in the tissue and media to the XAD®2 resin. At the end of this incubation period, the solid material from the suspension (which comprises both the resin and the ground tissue) is recovered by passing through a fine nylon mesh in order to achieve an initial, crude separation of the solid from the fluid phases. The remaining fluid phase is further processed by filtering through a polyethylene Buchner table-top funnel with a medium porosity fixed plate equipped with cellulose filter paper discs, thereby achieving the separation of any remaining solid materials (containing the tissue and resin) from the fluid phase.

The solid material retained in the filter paper is then recovered by carefully scraping it off the surface and it is then mixed with the crude nylon filtration retentate, which contains the ground tissue and XAD®2 resin with the adsorbed bioactives. This solid mixture is next subjected to an extensive wash with water to remove any fine particulates and other unbound materials using a Buchner funnel fitted with a cellulose filter paper. Finally, the washed solid mixture is then transferred into large, flat bed trays where excess moisture is removed using an air oven set at low temperature (30° C.) in preparation for extraction and preparation of technical.

The dried material is extracted by the addition of ethyl acetate, which yields raffinate (unextracted solids) and extract. The volume of this primary extract is reduced in a rotary evaporator to approximately 10% of its initial volume. The raffinate is then further extracted by the addition of methanol, thereby yielding secondary raffinate plus secondary extract. The latter is then evaporated to dryness and resuspended in the concentrated primary ethyl acetate extract. After rotary evaporation, this material produces the fraction referred to as "technical".

The technical is analyzed by HPLC separation in $C_{18}$ reverse phase columns, which reveals the presence of multiple limonoid species, including deacetyl-salannin, salannin, deacetyl-nimbin, azadiradione, and smaller amounts of azadirachtins A, B. D and H. At the end of the process, the yield of total limonoids (AZRLs) is determined by a colorimetric method. These technical fractions are biologically active, both in terms of antifeedant effects, as well as IGR activity.

The invention claimed is:

1. A bioreactor container, comprising:
   a container housing having a plurality of side portions, a bottom portion, and a top portion, wherein the top portion is sealably connectable to the plurality of side portions to define an internal chamber;
   an internal wall in at least one of the plurality of side portions that defines a media exchange aperture; and
   a mesh scaffolding disposable within the internal chamber of the container housing, wherein the mesh scaffolding further comprises:
      a series of alternating incline sections and decline sections each connected by a vertex, which form a plurality of channels spaced across the mesh scaffolding;
   wherein a relative position of the incline sections and decline sections are maintained by a support member that runs through opposing longitudinal edges of the mesh scaffolding.

2. The bioreactor container of claim 1, further comprising:
   a first tubing member sealably connectable to the media exchange aperture and extending inside the container housing; and
   a second tubing member sealably connectable to the media exchange aperture and extending outside the container housing.

3. The bioreactor container of claim 1, wherein the mesh scaffolding further comprising support members, which further include limiting members to contain movement of the mesh scaffolding along the support members.

4. The bioreactor container of claim 1, wherein the media exchange aperture is configured to dispense and suction culture media.

5. The bioreactor container of claim 2, wherein the first tubing member comprises an end portion that runs parallel to the internal wall.

6. The bioreactor container of claim 2, wherein the first tubing member comprises an end portion juxtaposed to a corner at the bottom portion of the container housing.

7. The bioreactor container of claim 1, wherein the media exchange aperture is only present on one of the plurality of side portions.

8. The bioreactor container of claim 1, wherein the bioreactor has a single media exchange aperture.

9. The bioreactor container of claim 1, wherein the top portion, when sealably connected to the plurality of side portions, is parallel to the bottom portion.

10. The bioreactor container of claim 1, wherein the mesh scaffolding is folded in an accordion-like fashion.

11. A method of growing hairy root tissue, comprising:
    placing a plurality of hairy root tissue samples on a bottom portion of the bioreactor container of claim 1;
    positioning a mesh scaffolding on top of the hairy root tissue samples so as to cover the samples, wherein the mesh scaffolding includes a series of alternating incline sections and decline sections each connected by a vertex, which form a plurality of channels spaced across the mesh scaffolding;
    sealing the internal chamber of the bioreactor container by releasably connecting a removable top portion to the plurality of side portions;
    adding a culture medium to the internal chamber of the bioreactor container through a tube sealably connected to a media exchange aperture formed by an internal wall in one of the plurality of side portions of the bioreactor container; and
    culturing the hairy root tissue samples.

12. The method of claim 11, further comprising moving the bioreactor container according to a motion profile.

13. The method of claim 12, further comprising adding an elicitor to the bioreactor container.

14. The method of claim 13, further comprising removing the hairy root tissue from the bioreactor container.

15. The method of claim 11, wherein the hairy root tissue samples are cultured for 3-12 weeks.

16. A system of bioreactor containers, comprising at least two bioreactor containers according to claim 1.

17. The system of bioreactor containers of claim 16, wherein each bioreactor container further comprises:
    a first tubing member sealably connectable to the media exchange aperture and extending inside the container housing; and
    a second tubing member sealably connectable to the media exchange aperture and extending outside the container housing.

18. A method of growing hairy root tissue, comprising:
    placing a plurality of hairy root tissue samples on a bottom portion of the bioreactor container of claim 1;
    positioning the mesh scaffolding on top of the hairy root tissue samples so as to cover the samples;
    sealing the internal chamber of the bioreactor container by releasably connecting a removable top portion to the plurality of side portions;
    adding a culture medium to the bioreactor container through a tube sealably connected to a media exchange aperture formed by an internal wall in one of the plurality of side portions of the bioreactor container;
    loading the bioreactor container onto an apparatus for stimulating plant cultures;
    moving the bioreactor containers on the apparatus according to a motion profile;
    and culturing the hairy root tissue samples.

19. The method of claim 18, further comprising adding an elicitor to the bioreactor container.

20. The method of claim 19, further comprising removing the hairy root tissue from the bioreactor container.

21. The method of claim 18, wherein the hairy root tissue samples are cultured for 3-12 weeks.

22. The method of claim 18, wherein the apparatus for stimulating plant cultures, comprises
- a frame including a support member;
- one or more trays movably connected to the support member;
- wherein each tray comprises:
  - a bottom portion having a first edge and a second edge;
  - a first flange member extending from the first edge above the bottom portion; and
  - a second flange member extending from the second edge above the bottom portion;
- wherein each tray is configured to move between a first angled position, where the first edge is below the second edge, and a second angled position, wherein the second edge is below the first edge; and
- a motion mechanism connected to the one or more trays and configured to move the one or more trays between the first angled position and the second angled position according to a motion profile configured to stimulate growth of the plant cultures.

* * * * *